United States Patent
Karason et al.

(10) Patent No.: US 7,037,283 B2
(45) Date of Patent: May 2, 2006

(54) CASTING PRODUCT AND METHOD FOR FORMING THE SAME

(75) Inventors: Gudjon G. Karason, Sollentuna (SE); Arni P. Ingimundarson, Reykjavik (IS)

(73) Assignee: Ossur hf, (IS)

( * ) Notice: Subject to any disclaimer, the term of this patent is extended or adjusted under 35 U.S.C. 154(b) by 154 days.

(21) Appl. No.: 10/681,224

(22) Filed: Oct. 9, 2003

(65) Prior Publication Data

US 2004/0077979 A1  Apr. 22, 2004

Related U.S. Application Data

(60) Provisional application No. 60/419,148, filed on Oct. 18, 2002.

(51) Int. Cl.
*A61F 5/00* (2006.01)

(52) U.S. Cl. .................................. 602/6; 602/8; 602/5

(58) Field of Classification Search ................. 602/5, 602/6, 7, 8; 428/294.7, 295.1, 297.4, 299.4; 442/63, 76, 79, 85, 108, 286, 164

See application file for complete search history.

(56) References Cited

U.S. PATENT DOCUMENTS

| | | | |
|---|---|---|---|
| 4,314,398 A | | 2/1982 | Pettersson |
| 4,454,874 A | | 6/1984 | Monnier |
| 4,537,184 A | * | 8/1985 | Williams, Jr. ................... 602/8 |
| 4,628,917 A | | 12/1986 | Campagna, Jr. et al. |
| 4,817,590 A | * | 4/1989 | Stancik, Jr. .................... 602/8 |
| 4,848,364 A | * | 7/1989 | Bosman ..................... 128/849 |
| 4,899,738 A | | 2/1990 | Parker |
| 4,928,678 A | * | 5/1990 | Grim .............................. 602/8 |
| 5,027,803 A | | 7/1991 | Scholz et al. |
| 5,318,504 A | | 6/1994 | Edenbaum et al. |
| 5,364,693 A | * | 11/1994 | Moren et al. ................ 442/164 |
| 5,449,550 A | * | 9/1995 | Yasis et al. .................. 442/180 |
| 5,480,376 A | | 1/1996 | Duback et al. |
| 5,520,621 A | | 5/1996 | Edenbaum et al. |
| 5,607,387 A | | 3/1997 | Martin et al. |
| 5,632,723 A | * | 5/1997 | Grim ........................... 602/19 |
| 5,637,077 A | | 6/1997 | Parker |
| 5,687,848 A | | 11/1997 | Scholz et al. |
| 5,700,409 A | * | 12/1997 | Corry .......................... 264/87 |
| 5,755,678 A | | 5/1998 | Parker et al. |
| 6,007,504 A | | 12/1999 | Bailey et al. |
| 6,066,107 A | * | 5/2000 | Habermeyer ................... 602/6 |
| 6,127,508 A | * | 10/2000 | Corley et al. ............. 528/111.3 |
| 6,132,835 A | | 10/2000 | Scholz et al. |
| 6,146,344 A | * | 11/2000 | Bader ............................ 602/6 |
| 6,152,892 A | * | 11/2000 | Masini .......................... 602/6 |
| 6,155,997 A | * | 12/2000 | Castro ......................... 602/27 |
| 6,254,959 B1 | * | 7/2001 | Hirano et al. ................. 428/71 |
| 6,353,077 B1 | * | 3/2002 | Shelvey ....................... 528/58 |
| 6,881,486 B1 | * | 4/2005 | Sendijarevic ............ 428/425.5 |

* cited by examiner

*Primary Examiner*—Henry Bennett
*Assistant Examiner*—Amanda Wieker
(74) *Attorney, Agent, or Firm*—Bacon & Thomas, PLLC

(57) ABSTRACT

A casting product for forming a hard structure about an object including a flexible fibrous substrate impregnated with a fluid-activated resin and a protective flexible casing surrounding the impregnated substrate. The casing includes a sealable passageway defined between the atmosphere and the interior of the casing, and is configured to permit injection of fluid, and removal of vapors and extant fluid with a vacuum from the casing.

7 Claims, 4 Drawing Sheets

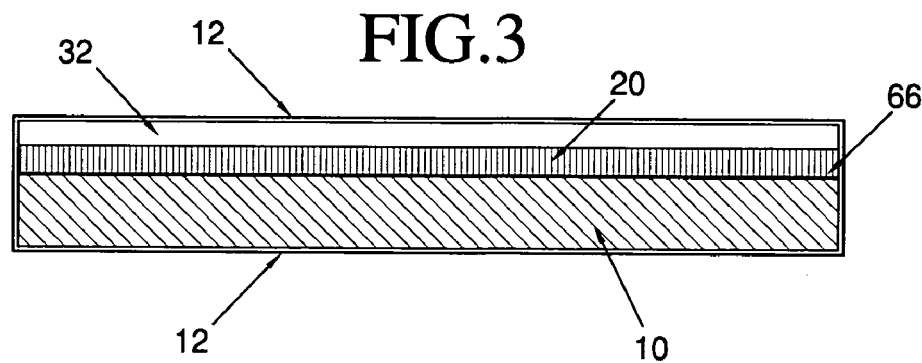
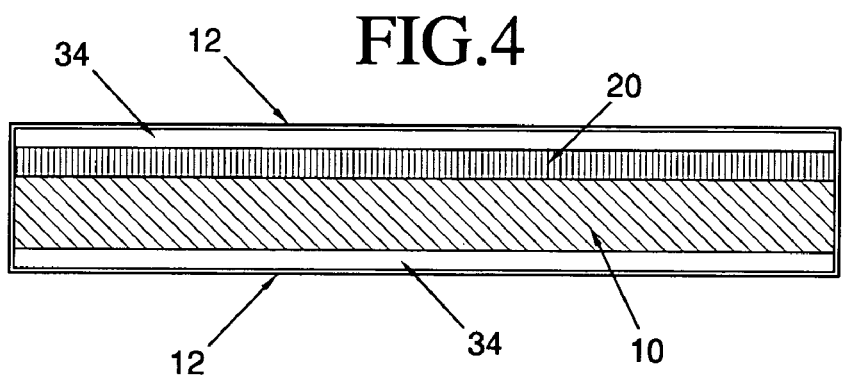
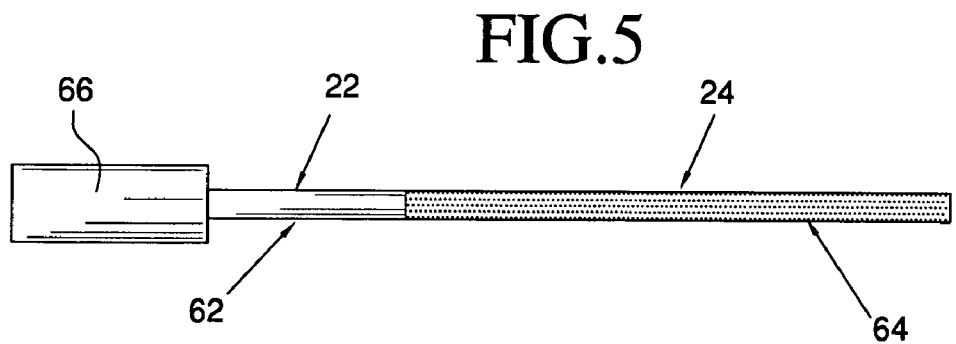

CASTING PRODUCT AND METHOD FOR FORMING THE SAME

This application claims the benefit of Provisional Patent Application Ser. No. 60/419,148, filed Oct. 18, 2002.

BACKGROUND OF THE INVENTION

1. Field of the Invention

The present invention relates generally to the field of casting products for orthopedic medicine and more specifically to the design of an improved casting method and apparatus for forming a hard structure about a body portion.

2. Background of Related Art Splints and medical casts are available for orthopedic purposes for the use in treatment of injuries to support and immobilize body portions. Typically, medical bandages are formed of a strip of fabric or scrim material impregnated with a substance which hardens into a rigid structure after the strip has been wrapped around a body member.

Traditionally, plaster of paris has been used as a hardening substance in fabricating a cast or splint upon an injured body portion. The cast is formed by initially applying a protective covering of a cotton fabric and then wrapping the body portion with a woven cloth impregnated with a plaster of paris which has been wetted by dipping in water immediately prior to application. Plaster of paris casts are widely utilized because of their low cost and their ability to conform to the contours of a body portion.

Plaster of paris casts, however, have a number of attendant disadvantages, including a low strength to weight ratio resulting in a cast which is bulky and heavy. In addition, plaster of paris casts develop their strength over an extended period of time, often requiring a period of 24 to 72 hours to develop full strength and therefore requiring the avoidance of weight bearing situations as the cast strengthens during this period. Plaster of paris casts also typically disintegrate in water, therefore making it necessary to avoid activities involving contact with water. Even if activities involving contact with water are avoided, perspiration over an extended period of time can break down the plaster of paris and create localized problems with odor and itching.

Plaster of paris casts also have numerous disadvantages related to the process of their fabrication. Specifically, the process of fabricating a plaster of paris cast is often very messy, time consuming, and requires multiple supplies and considerable skill. Wet casting material can get onto everything used in a casting environment from hands, clothes, patient, floor, furniture and the like.

In order to overcome the disadvantages of conventional plaster of paris casts, efforts have been made to provide a casting product having a plurality of layers of plaster of paris impregnated cloth. Such casting devices and methods of application thereof may enclose the casting material in sleeves or coverings of various materials so that direct contact with the casting material is not necessary (for example U.S. Pat. Nos. 4,235,228, 4,442,833, 4454,874 and 4,628,917). Some devices have attempted to provide measures which prevent moisture from the skin in the form of a moisture impervious layer next to the skin (U.S. Pat. No. 4,454,874). Other devices include a separate dry pad or layer which can be applied to the body portion after the casting material has been wetted (U.S. Pat. No. 4,628,917). Despite the noted efforts, plaster of paris casts still result in poor strength to weight ratios, and require an extended period of time to harden to full strength. Furthermore, even if wetting is avoided during the fabrication of the cast, perspiration over time may cause a breakdown in the plaster of paris or conversely if moisture impervious layers are used, such layers may restrict respiration.

An alternative to a plaster of paris cast is a synthetic cast which includes a flexible fabric impregnated with a curable resin that is hardened on the patient after the limb or body part to be splinted is wrapped with the fabric. Synthetic splints are generally lighter, more durable, and more water-resistant than plaster splints. However, resin used in synthetic splints is usually very sensitive to minute amounts of moisture and the resin can be activated simply by exposure to moisture in the atmosphere over a period of time.

Typically, synthetic splints are created from a resin impregnated fabric or substrate that is rolled into a coil and is dispensed from a dispensing box. Oftentimes, the impregnated substrate comprises woven fiberglass layers and is contained within a moisture impervious sleeve prior to use. In use, a portion of the resin impregnated substrate is separated from the coil and is exposed to water. The wetted impregnated substrate is then applied to a particular body portion. Before applying the resin impregnated substrate, however, a cushioning protective layer is generally disposed between the skin of the patient and the substrate.

During fabrication of a cast using the synthetic material, the resin can cause irritation to a patient because of migration of resin vapor and resin particles to the patients skin. In addition, fumes from the curing resin may cause irritation to the patient and individuals preparing the cast. Accordingly, there are environmental and health concerns related to the fabrication of synthetic casts not exhibited with plaster of paris casts. Another drawback in the utilization of woven fiberglass layers to form the substrate is that the hardened splint may not have consistent strength throughout all directions such that some fibers are more wetted than other fibers. Yet another drawback is that the thickness must be determined at the time of casting the splint and is not predetermined.

From the above discussion, it is readily apparent that both the traditional plaster of paris casting and the moisture-curable resin casting methods have advantages and disadvantages. On the one hand, plaster of paris casts are bulky, heavy in order to achieve the necessary strength, and difficult and messy to apply. On the other hand, moisture curable resins are very sensitive to the presence of moisture, the resin can cause sensory irritation to the patient and medical service providers, and the fiberglass may not have consistent strength due to inconsistent wetting of the resin.

SUMMARY OF THE INVENTION

It is an object of the invention to provide a casting product that presents a dry surface to the patient when applied.

It is further an object of the invention to provide a vapor-free casting product that contains and permits removal of vapors from curing resin without exposure to a patient.

It is yet another object of the invention to provide a casting product that is configured to permit injection of a liquid into an interior of the casting product.

It is yet another object of the invention to provide a casting product that is configured to permit removal of moisture contained therein with a vacuum.

It is yet another object of the invention to provide a casting product that does not require an external source of a fluid.

These and other objects and advantages of the present invention are achieved in one embodiment of the invention.

In one embodiment, a casting product for forming a hard structure about a body portion includes a flexible fibrous substrate impregnated with a fluid-activated resin and a protective, flexible casing. The casing is sufficiently configured to permit a vacuum to be drawn therein and includes a sealable passageway defined between the atmosphere and the interior of the casing.

The passageway is arranged to permit injection and removal of fluid from the casing so as to activate the resin and permit shaping of the impregnated fibrous substrate upon activation of the resin as the impregnated substrate is conformed to the object. In this manner, hardening of the substrate is achieved without the patient being exposed to the resin or the vapors therefrom and the substrate is compressed in a manner that ensures an even distribution of activated resin.

In one embodiment, the casting product includes a permeable breather disposed in the casing and positioned along at least one surface of the fibrous substrate in a substantially laminar relationship.

In another embodiment, the passageway includes an injection tube extending from the casing and an open end thereof is configured to couple to a fluid injection device and a vacuum. The tube includes a plurality of holes defined along a distal portion thereof.

In another embodiment, the casting product includes a liquid containment pouch disposed in the casing and positioned along a surface of the breather in a substantially laminar relationship with the breather and substrate.

In another embodiment, a sealed aperture defines the sealable passageway wherein the sealed aperture is perforated so as to enable facile puncturing thereof with a fluid injection device.

These and other important aims and objects of the present invention will be further described by reference to the accompanying drawings, description and claims.

BRIEF DESCRIPTION OF THE DRAWINGS

FIG. 3 is a cross-sectional view of the casting product of FIG. 2 with a water pouch.

FIG. 4 is a cross-sectional view of the casting product of FIG. 3 with an additional water pouch.

FIG. 5 is a plan view of a tube having a plurality of apertures.

DETAILED DESCRIPTION OF THE INVENTION

Figure 1:
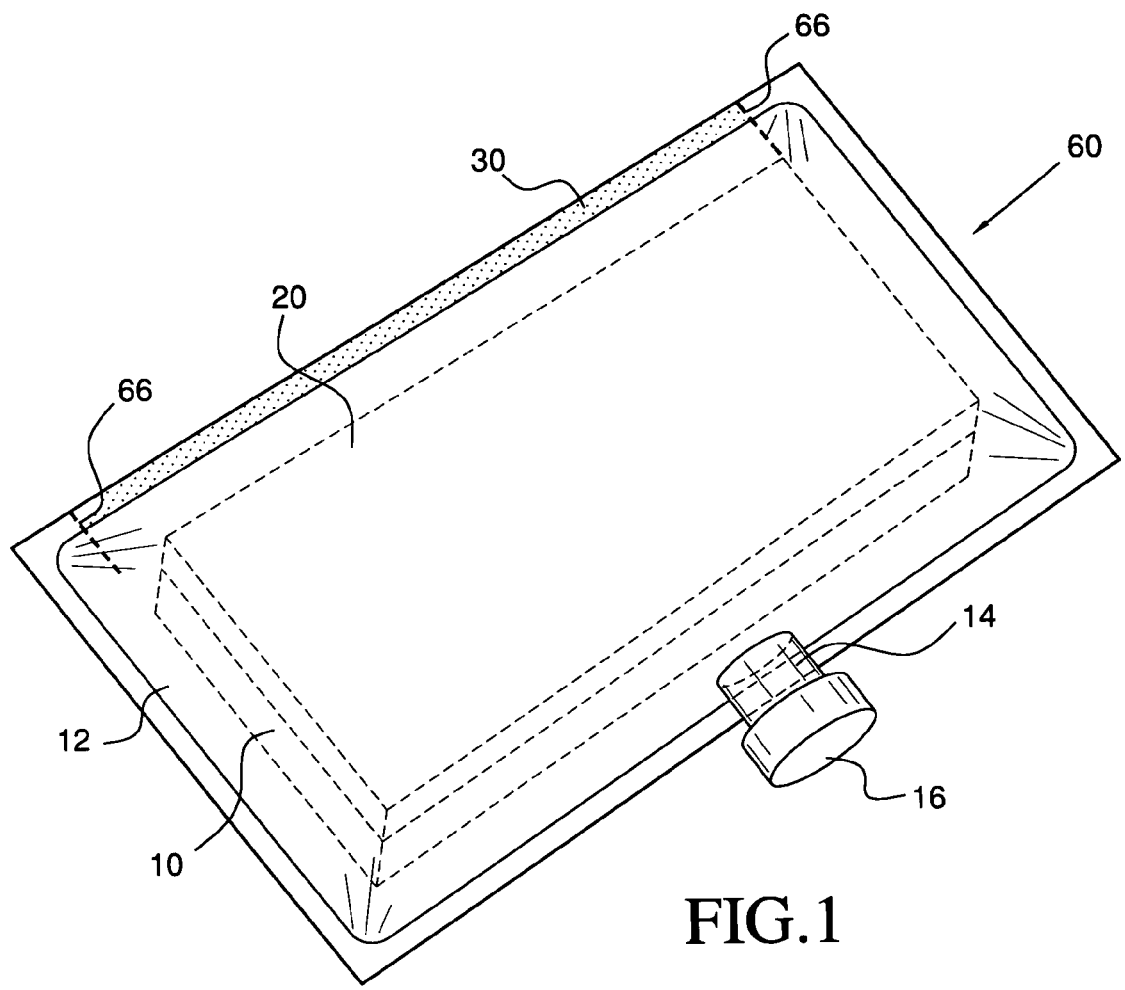
FIG. 1 is a perspective view of the casting product sealed from the atmosphere.

Referring now specifically to the drawings, a casting product 60 is shown in FIG. 1. Casting product 60 can be sold in any particular size or form suitable for forming a hard structure about an object, whether for the preferable use in the immobilization of a body portion, structural member or any other type of object of an appropriate scale that permits application of a manipulable casting product.

Casting product 60 includes a flexible fibrous substrate 10 impregnated with a resin activated by a predetermined fluid such as air or water. In the embodiment discussed herein, water is used as the predetermined fluid. The substrate 10 is preferably comprised of a suitable number of overlaid layers of a woven or knitted relatively open fabric or mesh. The substrate 10 is impregnated with a resin in generally a reactive system which remains stable when maintained in substantially moisture-free conditions but which hardens upon exposure to sufficient moisture to form a rigid, self-supporting structure.

In one embodiment, the resin is a polyurethane resin, however, it is possible to use other types of resin as long as hardening or activation can be controlled.

In one embodiment woven fiberglass may be used as the substrate 10, however other materials may be suitable as a substrate such as woven polyester, spandex, carbon fibers and KEVLAR. Alternatively, the substrate 10 can be formed of a single layer of non-woven material not limited to the above-mentioned materials, including randomly disposed fibers forming multiple intersections therebetween to thereby increase the resistance of a hardened casting product to forces exerted in different directions.

The substrate 10 is enclosed by casing 12 which defines a pouch that is used to enclose the substrate 10, permit the injection of liquid water used to react with the resin, contain vapors from curing resin, and withstand the pull of a vacuum used to remove vapors extant therein. The casing 12 protects the substrate 10 from excessive exposure to moisture in the atmosphere and is formed of a material that is flexible. In a preferred embodiment, the casing is moisture impervious. Since the casing may contact the skin of a body portion during casting, the casing 12 should be formed from a material that will not cause skin irritation and which will conform to a body portion outline.

The casing 12 may be formed from a variety of different materials including a flexible polymer film including silicone, polyurethane or polyester, or a textile coated with any of these suitable materials. The casing may be welded or adhered along seams of the selected material as shown in FIG. 1 by seams 30.

While the casing is described as moisture impervious in a preferred embodiment, it will be understood that the casing may alternatively be moisture permeable. In this alternative embodiment, it is preferable that the casing be moisture permeable so as to allow perspiration to evaporate through the casting product. While this alternative casing may be moisture permeable, it should be sufficiently woven or have a sufficiently tight porosity to permit a suitable, near vacuum environment to be drawn therein when forming the casting product. Furthermore, the casing should be configured to sufficiently retain a liquid used to activate the substrate.

In the preferred embodiment, the casing 12 defines a hermetically sealable passageway 14 which communicates, when unsealed, between the atmosphere and the interior of the casing 12. In this embodiment, the passageway 14 is a sealable tube defined by the casing 12. Prior to activation of the resin in the substrate 10, the interior of the casing 12 is sealed from the atmosphere with cap 16 positioned at the end of the tube 14.

Although the passageway 14 is illustrated in FIG. 1 as a tube, the passageway 14 may consist of any suitable means configured to permit the introduction of water into the casing and removal therefrom with a vacuum. More specifically, examples of the passageway 14 include a sealed aperture defined along the casing 12 which is perforated yet still hermetically seals the casing 12 and permits facile puncturing by a fluid injection device or vacuum, or a zipper disposed along the casing and of which permits the interior of the casing to be hermetically sealed. Alternatively, the passageway 14 may be created by puncturing the casing to form an aperture when it is desired to activate the resin of the substrate 10.

Figure 2:
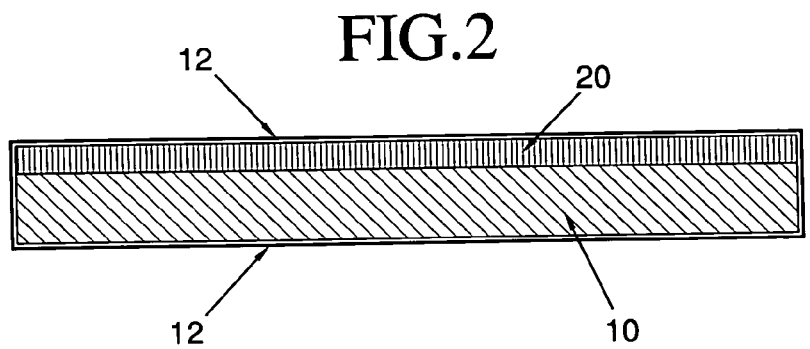
FIG. 2 is cross-sectional view of the casting product with a breather.

A breather 20 is illustrated in FIGS. 1 and 2 as being disposed along a surface of the substrate in a generally laminar relationship. The breather 20 includes a plurality of holes or passages within which water vapor and liquid water may freely pass. Preferably, the breather 20 is formed of a hydrophobic fabric so that the breather 20 does not absorb liquid water intended for use in activating the resin impregnated in the substrate 10. The breather 20 can be formed of any porous material which will permit passage of liquid water therethrough so as to distribute water across the substrate 10.

As shown in FIG. 3, a layer of release film 66 is disposed between the substrate 10 and breather 32. The release film 66 facilitates removal of the breather 20 from the substrate 10 when the casing 10 requires removal.

FIG. 3 illustrates in cross-section a liquid containment pouch 32 which is disposed within the casing 12 in a generally laminar relationship to the substrate 10 and the breather 20. This liquid containment pouch 32 is made of a fluid impervious material, such as a plastic, and may be ruptured by pressure or otherwise opened so as to allow liquid, such as water, contained therein to distribute over the breather 20 and onto the substrate 10 to activate the resin.

FIG. 4 illustrates in cross-section a heat isolator layer 34 which is disposed within the casing 12 in a generally laminar relationship to the substrate 10 and the breather 20. The heat isolator layer 34 is depicted as being positioned -along a surface of the substrate 10 opposite to the breather 20. The heat isolator layer 34 is arranged to insulate the body portion against heat generated from the curing resin of the substrate 10. The heat isolator layer 34 can also serve as a padding layer that will conform to a body portion.

Figure 7:
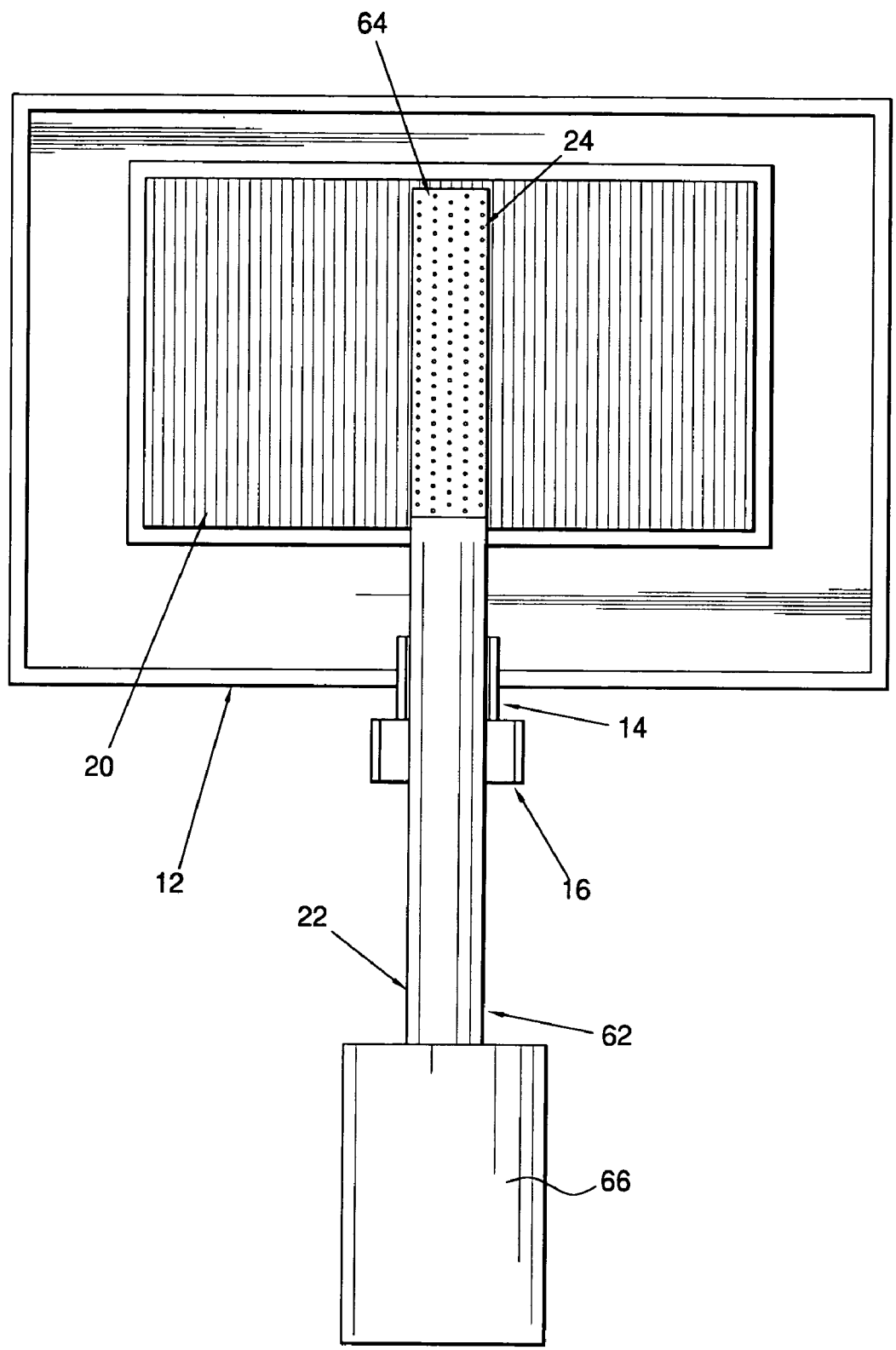
FIG. 7 is a plan view of the casting product connected to the tube of FIG. 5 connected to a resin moisturizing and removal device.

FIG. 5 illustrates an injection tube 22 configured to be inserted into the passageway 14 shown in FIG. 1. The injection tube 22 includes a plurality of apertures 24 defined along a distal portion thereof. As shown in FIG. 7, the injection tube 22 is dimensioned and configured so that the distal portion 64 having apertures 24 extends sufficiently into the casing 12 so as to distribute water across the substrate 10. The tube 22 is also arranged such that a proximal portion 62 not having the apertures 24 extends outwardly from the passageway 14. The proximal portion 62 of the tube 22 is configured so as to receive a fluid injection device or a vacuum device, collectively identified as reference numeral 66.

Figure 6:
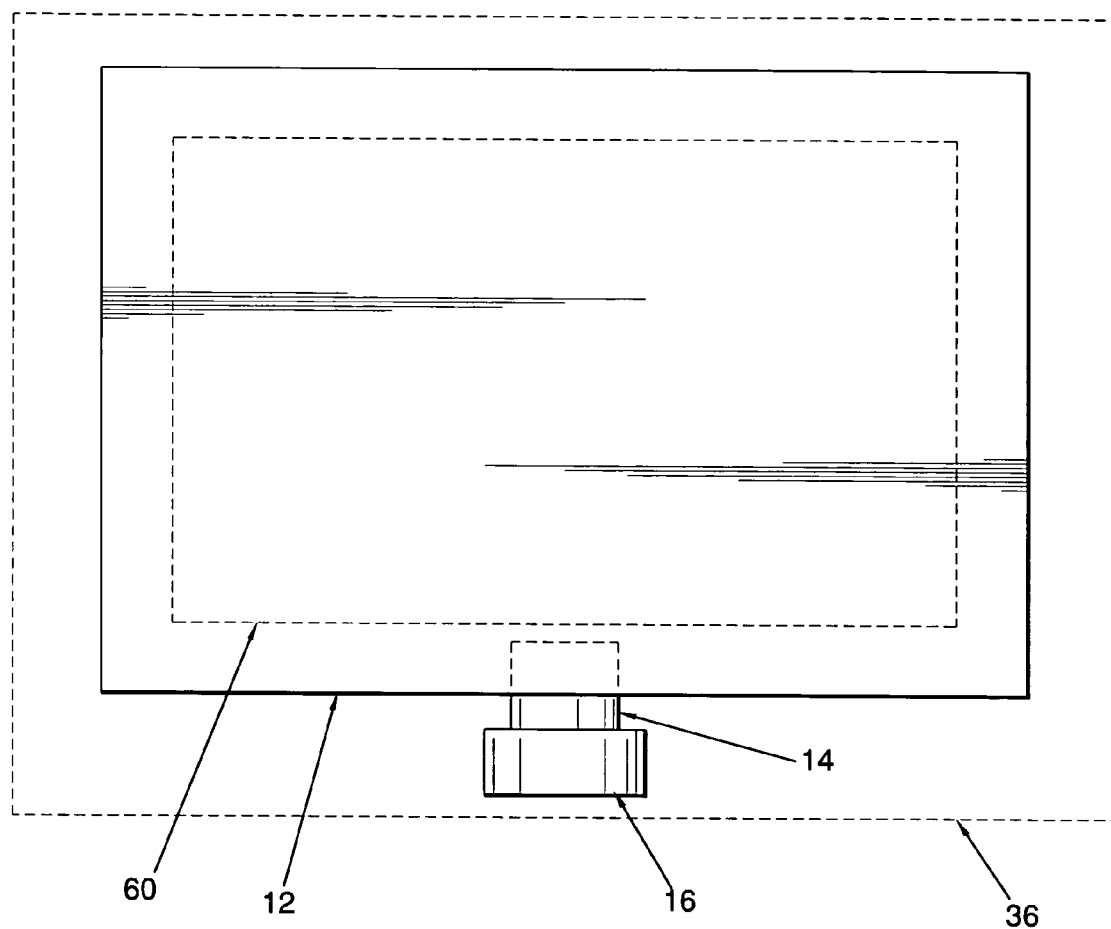
FIG. 6 is a plan view of the casting product in a fluid impervious pouch.

FIG. 6 depicts the casing 12 within a protective envelope 36. The envelope 36 is preferably formed of aluminum foil, or any other suitable moisture-impervious material. The protective envelope 36 serves to protect the casing product 60 to prevent the premature hardening of resin and therefore prolong the storage of the casing product. The envelope 36 is preferably formed by either sealing the peripheral edges thereof or connecting the edges of the foil along a single seam. Accordingly, any type of sealing arrangement of the aluminum foil envelope 36 is suitable as long as the sealing serves to prevent entry of moisture.

In turning to the method of fabricating the casing product, the casing product of the present invention is made by impregnating fibrous substrate 10 with a resin. Before impregnation with a water activated resin, the substrate 10 must be free of any moisture and it is therefore preferable that the substrate 10 be kept in a dry room or desiccator prior to impregnation. Furthermore, it is necessary that the impregnation of the substrate 10 with the resin be conducted in an environment free of moisture.

The substrate 10 is impregnated with a resin constituting a free flowing, uncured semi-viscous liquid. In one embodiment, the resin is a polyurethane resin however, it is possible to use other types of resin as long as hardening or activation can be controlled. After the substrate 10 has been impregnated with a resin, a breather 20 is positioned along one side of the substrate so as to ease the flow of water into the impregnated substrate 10 and to also aid in the evacuation of air during casting.

Referring to FIG. 1, the impregnated substrate 10 and breather 20 are placed inside a generally protective moisture impervious casing 12 having an opening 66 configured to permit insertion of substrate 10 and breather 20, and a hermetically sealable passageway 14 incorporated therein which defines a passageway between the interior of the casing and the atmosphere. The casing opening 66 is sealed along the periphery thereof to prevent exposure of the substrate 10 to moisture. In the event there is excess air within the sealed casing, a vacuum is used to draw the air from the interior of the casing. As shown in FIG. 6, the casing 12 is positioned within a protective envelope 36 so as to provide additional protection from moisture and permit prolonged storage of the casting product 60.

As illustrated in FIG. 1, the method may further include the step of positioning the breather 20 along a surface of the substrate 10 such that the breather 20 permits passage of liquid water therethrough so as to distribute water across the substrate 10.

Alternatively, the substrate 10 is placed into the casing 12 prior to impregnation of the resin. In this instance, the resin is injected into the casing 12 and penetrates the substrate 10 therein. Furthermore, a vacuum device can be used to draw any remaining moisture or fumes from the resin present within the casing 12 to more effectively urge penetration of the resin in the substrate 10 and dispose of the extant fumes and moisture in the casting product.

As an alternative to the above mentioned, the resin is activated by directing UV light towards the substrate 10. The step of directing UV light towards the substrate 10 serves to replace the step of injecting water to activate the resin. It should be noted, however, that a vacuum device can still be employed after activation of the resin with UV light in order to ensure that the resin is uniformly distributed throughout the substrate 10 to ensure optimal strength of the resulting product.

In an alternative embodiment, the vacuum is achieved by a suction cup which is placed over the passageway 14. In this instance, the passageway 14 comprises a hole or puncture in the casing 12. According to this embodiment, tubing is not necessarily required since the suction cup may directly connect to the casing. It should be noted, however, that a tube could be used to connect the hole or puncture to the suction cup. This embodiment is particularly useful if the resin is activated by UV light.

The method according to the present invention for applying the casting product 60 to a body portion comprises the steps: of inserting an injection tube 22 having a plurality of apertures defined along a distal portion 64 thereof into the casing 12, injecting water through the passageway 14 with a fluid injection device 26, preferably a syringe, and into the casing 12 to activate the resin impregnated into substrate 10; removing excess water from the casing 12 with a vacuum device 28 connected to the passageway 14 after the resin has been activated; applying the casing 12 to a body portion to conform the impregnated substrate 12 to the shape of a body portion; and allowing the resin to harden to preserve the configuration of the casting product 60 defined by the body portion.

Upon the curing of the resin, one can remove the casing 12 from the formed substrate 10.

Alternatively, the method includes the step of conforming the casting product 60 to the body portion with the vacuum device 28 being used to compress the substrate and remove vapors and excess resin simultaneously. In this instance, the vacuum device 28 effectively conforms the shape of the casting product 60 to the body portion.

As an alternative to the above method, the method includes the step of placing the casting product 60 over a body portion prior to activating the resin and leaving the casting product 60 over the body as the casting product is cured to shape.

The combination of materials and method according to the present invention have now been described with reference to the described embodiments thereof. It will be appreciated by those skilled in the art that certain substitutions of materials and the use of slightly modified method steps are possible without departing from the spirit of the invention. Thus, the scope of the invention should not be limited to the disclosed product and method steps described in this application, but only to products and method steps described by and included in the language of the claims and their equivalents.

We claim:

1. A kit for forming a hard structure about an object comprising:
   a flexible fibrous substrate impregnated with a resin and a protective flexible casing surrounding said impregnated substrate and including a sealable passageway defined between the atmosphere and the interior of said casing;
   an injection device configured to be received by said passageway and enabling injection of fluid into said casing, said resin being activated by the fluid injected into said casing by said injection device; and
   a vacuum configured to be received by said passageway, said vacuum connected to said passageway and enabling removal of excess fluid in said casing after fluid used to activate the resin is injected by said injection device.

2. The kit according to claim 1 wherein said injection device includes a syringe.

3. The kit according to claim 1 wherein said injection device includes a pipe having a plurality of holes defined along a distal portion thereof, said distal portion configured to be inserted through said passageway and into said casing interior.

4. The kit according to claim 1 wherein the casing is at least substantially moisture impervious.

5. A method of immobilizing a body portion with a casting product including a flexible fibrous substrate impregnated with a fluid-activated resin and a protective flexible casing surrounding said impregnated substrate and including a sealable passageway defined between the atmosphere and the interior of said casing, said method comprising the steps of:
   injecting fluid through said passageway and into said casing to activate said resin;
   removing excess fluid from said casing with a vacuum connected to said passageway after said resin has been activated;
   applying said casing to a body portion to conform the impregnated substrate to the shape of a body portion; and
   allowing the resin to harden to preserve the configuration defined by the body portion.

6. The method according to claim 5 further comprising the step of inserting an injection tube having a plurality of apertures defined along a distal portion thereof, said distal portion configured to be inserted through said passageway and into said casing.

7. The method according to claim 6 wherein said distal portion of said injection tube is positioned across a breather disposed along a surface of said substrate.

* * * * *